United States Patent
Rencoret et al.

(10) Patent No.: US 11,786,111 B2
(45) Date of Patent: Oct. 17, 2023

(54) PROBE DEPLOYMENT DEVICE

(71) Applicant: Imperial College Innovations Limited, London (GB)

(72) Inventors: Fernando Basilio Avila Rencoret, London (GB); Daniel Stuart Elson, London (GB); George Mylonas, London (GB)

(73) Assignee: Imperial College Innovations Limited, London (GB)

( * ) Notice: Subject to any disclaimer, the term of this patent is extended or adjusted under 35 U.S.C. 154(b) by 496 days.

(21) Appl. No.: 15/555,945

(22) PCT Filed: Mar. 6, 2015

(86) PCT No.: PCT/EP2015/054794
§ 371 (c)(1),
(2) Date: Sep. 5, 2017

(87) PCT Pub. No.: WO2016/141962
PCT Pub. Date: Sep. 15, 2016

(65) Prior Publication Data
US 2018/0042457 A1   Feb. 15, 2018

(51) Int. Cl.
*A61B 1/00*       (2006.01)
*A61B 1/31*       (2006.01)
(Continued)

(52) U.S. Cl.
CPC .......... *A61B 1/0016* (2013.01); *A61B 1/0014* (2013.01); *A61B 1/00082* (2013.01); (Continued)

(58) Field of Classification Search
CPC . A61B 10/04; A61B 1/00082; A61B 1/00087; A61B 1/00096; A61B 1/00101;
(Continued)

(56) References Cited

U.S. PATENT DOCUMENTS 6,152,870 A * 11/2000 Diener ................. A61B 1/0008
600/104
6,175,751 B1 * 1/2001 Maizes ............. A61B 5/14542
600/338
(Continued)

FOREIGN PATENT DOCUMENTS

EP    1701660    8/2005
EP    1726247    11/2006
(Continued)

OTHER PUBLICATIONS

Medical Enginerring Centres Annual Meeting and Bioengeineering 2014: The poster was shown at 10:55 AM, Wednesday Sep. 10, 2014, during that event, at the college. 1 page.
(Continued)

*Primary Examiner* — Yi-Shan Yang
*Assistant Examiner* — Alexei Bykhovski
(74) *Attorney, Agent, or Firm* — Lee & Hayes, P.C.; Bea Koempel-Thomas (57) ABSTRACT

The present disclosure relates to an apparatus for mounting on a guide member for insertion into an anatomical cavity, the apparatus comprising a body defining a cavity for receiving a guide member therethrough, a drive arrangement for moving the body along a guide member disposed through the body, a probe secured to the body for, in use, obtaining a measurement from, taking a sample of, applying a substance to, or applying a therapy to, an environment of the body, and a measurement arrangement for measuring a position relative to the guide member disposed through the body.

34 Claims, 4 Drawing Sheets

(51) Int. Cl.
  *A61B 5/00* (2006.01)
  *A61B 10/04* (2006.01)
  *A61M 25/10* (2013.01)

(52) U.S. Cl.
  CPC ...... *A61B 1/00087* (2013.01); *A61B 1/00096* (2013.01); *A61B 1/00101* (2013.01); *A61B 1/00135* (2013.01); *A61B 1/00154* (2013.01); *A61B 1/00156* (2013.01); *A61B 1/00165* (2013.01); *A61B 1/31* (2013.01); *A61B 5/0075* (2013.01); *A61B 5/0084* (2013.01); *A61B 5/4255* (2013.01); *A61B 5/4839* (2013.01); *A61B 5/6853* (2013.01); *A61B 5/6858* (2013.01); *A61B 10/04* (2013.01); *A61M 25/1002* (2013.01)

(58) Field of Classification Search
  CPC .............. A61B 1/00135; A61B 1/0014; A61B 1/00154; A61B 1/00156; A61B 1/0016; A61B 1/00165; A61B 1/31; A61B 5/0075; A61B 5/0084; A61B 5/4255; A61B 5/4839; A61B 5/6853; A61B 5/6858; A61M 25/1002
  See application file for complete search history.

(56) References Cited

U.S. PATENT DOCUMENTS

| | | | |
|---|---|---|---|
| 9,125,562 B2* | 9/2015 | Spencer | A61B 5/6852 |
| 2003/0187347 A1 | 10/2003 | Nevo et al. | |
| 2004/0233193 A1* | 11/2004 | Margadant | G06T 15/08 |
| | | | 345/419 |
| 2005/0096647 A1* | 5/2005 | Steinke | A61B 18/1815 |
| | | | 606/41 |
| 2006/0195014 A1 | 8/2006 | Seibel et al. | |
| 2009/0270702 A1* | 10/2009 | Zeng | A61B 5/0075 |
| | | | 600/323 |
| 2011/0065988 A1* | 3/2011 | Eidenschink | A61B 1/00151 |
| | | | 600/115 |
| 2011/0230712 A1 | 9/2011 | Matsuura et al. | |
| 2011/0288374 A1 | 11/2011 | Hadani et al. | |
| 2012/0289974 A1* | 11/2012 | Rogers | A61B 34/30 |
| | | | 606/130 |
| 2012/0316419 A1* | 12/2012 | Chevalier | A61B 5/02007 |
| | | | 600/381 |
| 2013/0109957 A1 | 5/2013 | 'T Hooft et al. | |
| 2013/0172679 A1 | 7/2013 | Ashida et al. | |
| 2014/0276391 A1 | 9/2014 | Yu | |
| 2016/0235400 A1* | 8/2016 | Hiernaux | A61B 17/0469 |

FOREIGN PATENT DOCUMENTS

| | | |
|---|---|---|
| EP | 1870031 | 12/2007 |
| GB | 1316333.2 | 9/2013 |
| JP | H0467831 | 3/1992 |
| JP | 2005230444 | 9/2005 |
| JP | 4810623 B2 | 11/2011 |
| JP | 2011227132 | 11/2011 |
| JP | WO2011016428 | 1/2013 |
| WO | WO07131177 | 11/2007 |

OTHER PUBLICATIONS

PCT Search Report and Written Opinion for corresponding PCT International Application No. PCT/EP2015/054794 dated Jan. 12, 2016, 19 pages.
Japanese Notice of Reasons for Refusal for corresponding Japanese Patent Application No. JP2017546987 dated Jan. 8, 2019, 8 pages.

* cited by examiner

PROBE DEPLOYMENT DEVICE

FIELD OF THE INVENTION

The present invention relates to an apparatus for use in endoscopy. In particular, but not exclusively, the present invention relates to a device arranged to move along an endoscope and deploy one or more probes, arranged to sample or treat the interior of a tubular lumen, along a direction radially outwards from the endoscope.

BACKGROUND

The presence of abnormal lesions in the tissue of a tubular organ, the colon for example, can signify certain types of cancer. It is therefore important to identify and classify all the abnormal lesions present in such tissue. Methods of scanning for these abnormal lesions traditionally involve the use of endoscopes or endoscopic capsules. Usually, the location of each lesion is identified using the endoscope or endoscopic capsule, before a biopsy of each lesion is taken for histopathological examination. However, this method often does not identify all the lesions present in the tissue; for example, up to 22% of pre-cancerous lesions in a patient can be missed during a colonoscopy and may develop into colorectal cancer.

Optical biopsy techniques (e.g. confocal laser endo-microscopy (CLE) or multi-photon microscopy) aim to reduce or eliminate the need for taking physical biopsies by using high magnification images to identify lesions and perform histopathological diagnosis. However, the equipment is complex and expensive and the use of optical biopsy techniques lengthens the duration of a procedure, increasing both cost and patient discomfort.

Optical spectroscopy techniques such as diffuse reflectance spectroscopy (DRS) can detect areas of suspicious tissue using cheap and simple hardware, but lack the high magnification required to perform histopathological diagnoses. Suspicious areas are identified for further investigation or biopsy using multispectral imaging. In multispectral imaging, an optical signature of tissue is determined. This signature is a spectral response to applied broadband light and is dependent on how the different wavelengths of light are reflected from the surface of the tissue. Thus, by illuminating tissue with broadband light and determining the spectral response, normal tissue can be differentiated from pre-malignant tissue.

These spectroscopic methods use single point probes (i.e. one pixel) for imaging. With single point probes, it is difficult to gather two-dimensional information or generate images of large areas, for example the colon. There is therefore a need for a device which may facilitate the identification of more lesions than conventional endoscopes, whilst providing better, quicker and cheaper procedures than current optical techniques.

SUMMARY

According to a first aspect, there is provided an apparatus for mounting on a guide member for insertion into an anatomical cavity. The apparatus comprises a body defining a cavity for receiving a guide member therethrough and a drive arrangement for moving the body along a guide member disposed through the body. A probe is secured to the body for, in use, obtaining a measurement from, taking a sample of, applying a substance to, or applying a therapy to, an environment around the body. The apparatus further comprises a measurement arrangement for measuring a position of the body relative to the guide member disposed through the body.

In embodiments where the guide member is an endoscope, by moving the body (and thus the probe) along the endoscope, the probe can take measurements of or apply substances to the cavity in which the endoscope is deployed without using one of the existing endoscope instrument channels or requiring any movement of the endoscope itself. These instrument channels can therefore be used concurrently with the probe. For example, the probe could scan a section of the cavity and then biopsies could be taken from any lesions identified by the scan whilst the probe continues to scan a different section of the cavity. The apparatus may therefore facilitate both diagnoses and therapy in one procedure, and reduce the duration and the cost of a procedure. In embodiments where the guide member is not an endoscope and, for example, is inserted into anatomical sites other than the gastrointestinal tract, the body can be moved along the guide member to image, or apply a treatment to the inside of tubular other structures such as blood vessels.

The drive arrangement may comprise a mechanism secured to the body for applying a driving force to the guide member disposed through the body to drive the body along the guide member. The drive arrangement may comprise one or more rotating members coupled to the body and arranged to engage the guide member to move the body along the guide member. In some embodiments, the one or more rotating members are arranged to move the body along the guide member by frictional engagement of the guide member. In other embodiments, the one or more rotating members are configured as a pinion or a worm gear, the pinion or worm gear being arranged to move the body along the guide member by engaging a rack surface on the guide member.

The rack surface can be formed directly on the guide member or can be incorporated into a sheath which covers the guide member. The sheath may be disposable. The rack surface on the guide member or the sheath provides teeth, which are arranged to mesh with teeth on the one or more rotating members to form a rack and pinion. Alternatively, in other embodiments, the one or more rotating members 112 are configured as a worm gear arranged to engage the rack surface. In some embodiments, the sheath may not have a rack surface, but may instead provide sufficient traction for the one or more rotating members to translate the device along the guide member by frictional engagement. In other embodiments, the guide member itself provides the traction for the one or more rotating members to translate the device along the guide member by frictional engagement.

In some embodiments, the drive arrangement comprises a capstan and a tendon engaging the capstan for actuating the drive arrangement. This arrangement is advantageous as it can reduce the complexity of the apparatus, reducing the cost of, for example, an endoscopic procedure. In some embodiments, each of the one or more rotating members comprises a capstan. Alternatively, only some of the one or more rotating members comprise a capstan. The capstan or capstans may be directly or indirectly coupled to one or more of the one or more rotating members. In some arrangements, there may be a single capstan and a single tendon for actuating the capstan, wherein the capstan and tendon drive a plurality of rotating members. In other embodiments, the drive arrangement comprises an electric motor for actuating the drive arrangement. This could be advantageous as it may facilitate remote deployment and operation of the apparatus. The motor may be directly coupled to the one or more rotating members or indirectly coupled to the one or more rotating members, for example via a gear box or other components. Preferably, the motor is a micro electric motor. This may facilitate a reduction in apparatus weight and size.

In some embodiments, the drive arrangement comprises a transmission member coupled to the body and arranged to move the body relative to the guide member disposed through the body in response to a force applied to the transmission member. The transmission member may comprise a sheath for accepting the guide member, wherein the sheath is sufficiently stiff axially to translate the body relative to the guide member disposed through the body. Furthermore, in some embodiments the sheath can be sufficiently rigid torsionally to rotate the body relative to the guide member disposed through the body. The sheath may have one or both of these properties. The use of a transmission member may reduce the complexity of the apparatus. If the cost of the apparatus is sufficiently reduced, the apparatus could be used as a disposable tool, meaning it is replaced between each procedure. This may have benefits such as a lower cost, as the decontamination process required for used tools can be very expensive, and the possible benefit of a lower risk of patients acquiring infection. The transmission member and the body may be directly coupled. Alternatively, there may be provided a coupler for coupling the transmission member and the body.

According to a second aspect, there is provided an apparatus comprising a guide member for insertion into an anatomical cavity and a probe deployment arrangement for deploying a probe radially outwards from the guide member. The probe deployment arrangement can be incorporated into the guide member itself. This could be advantageous, as it could allow the probe deployment arrangement to be fully integrated into the guide member, removing or reducing the need for tendons or wires external to the guide member.

According to a third aspect, there is provided an apparatus for attaching to a guide member for insertion into an anatomical cavity. The apparatus comprises a probe deployment arrangement for deploying a probe radially outwards from the guide member.

This apparatus may be advantageous as the probe deployment arrangement can be removed from the guide member and could therefore be a disposable item, conferring the advantages previously discussed, such as a lower cost. For example, there is no decontamination process required for the apparatus after use. Advantageously, the third aspect of the device can be combined with the first aspect to provide the ability to move the probe deployment arrangement along the guide member. The apparatus may further comprise a probe secured to the probe deployment arrangement for, in use, obtaining a measurement from, taking a sample of, applying a substance to, or applying a therapy to, an environment of the probe.

The probe deployment arrangement may be configured to deploy the probe along a direction radially outwards from a longitudinal axis of the guide member. Advantageously, the apparatus of the second and third aspects may facilitate the probe being deployed at a preferred orientation to be in good contact with the tissue forming the wall of the cavity in which the guide member is deployed (e.g. with the probe surface being substantially parallel to the lumen surface). With the described probe deployment mechanism, this good contact between the probe and the cavity wall may be achieved for a range of shapes and sizes of the tubular organ. This may facilitate improved scanning results.

In some embodiments of the apparatus of the second and third aspects, the apparatus comprises a drive arrangement for moving the probe relative to the guide member. This may facilitate the scanning of an increased area of the cavity in which the guide member is deployed, without requiring the movement of the guide member to which the apparatus is attached to or incorporated into. As described above, the second aspect can be combined with the drive arrangement of the first aspect to facilitate the movement of the probe by facilitating the movement of the entire apparatus along the guide member. This may facilitate diagnosis and therapy in one procedure. When the guide member is an endoscope, the entire lumen, such as the colon, can be scanned and then the endoscope can be moved to biopsy or resect any suspicious areas. Alternatively, the lumen can be scanned whilst the endoscope channels are being used to biopsy another area. When the guide member is inserted into a tubular structure such as a blood vessel, the apparatus can, for example, travel along the guide member and repair the internal lining of the vessel in a single procedure.

In other embodiments, the apparatus of the first aspect of the device may further comprise a probe deployment arrangement for deploying the probe radially outwards from the guide member. Deploying the probe radially outwards from the guide member may comprise deploying the probe along a direction radially outwards from a longitudinal axis of the guide member. The apparatus of this embodiment can be moved along the guide member to the desired position and the probe can then be deployed in a way that may facilitate an improved orientation of the probe with respect to the wall of the cavity, as discussed above.

In some embodiments, applicable to all the above aspects, the probe deployment arrangement comprises a resilient member arranged to maintain a pressure between the probe and a wall of the cavity in which the guide member is deployed. This may facilitate the pressure between the probe and the wall remaining both relatively constant and at a level below a safe pressure threshold of the cavity. Maintaining a pressure with the wall may allow the probe to work more effectively and may facilitate the obtainment of results which are more comparable between different areas of the cavity, in particular if the output of the probes is sensitive to the pressure applied to them.

In some embodiments, the resilient member could be an active loading system, actuated by, for example, hydraulics or pneumatics. In an active system, the resilient member could further comprise pressure or strain sensors. These sensors may facilitate measuring the force between the probe and cavity wall. The actuation of the resilient member could then be changed, based on the output of the pressure or strain sensors, to prevent the pressure on the wall of the cavity exceeding the prescribed safety threshold. In other embodiments, the resilient member can be a passive spring loading system, which may facilitate the prevention of pressures on the cavity wall that exceed the safety threshold level. Preferably, the resilient member should not allow a pressure on the cavity wall to exceed a tolerable threshold and ideally, the resilient member should apply pressures to the cavity wall that are much lower than the safety threshold.

In some embodiments, the probe deployment arrangement comprises a plurality of bars connected in a parallel linkage, the plurality of bars being arranged to move the probe along a direction radially outwards from the longitudinal axis of the guide member when the probe deployment arrangement is actuated. The actuation of the parallel linkage can be varied to change the displacement of the probe along a direction radially away from the guide member. This arrangement may facilitate adaptation of the device to the diameter of and/or conformity to the shape of the tubular organ in which the guide member is deployed.

Actuation of the probe deployment arrangement can be mechanical, pneumatic or a hydraulic. Actuation can be by, for example, a motor. In some embodiments, the motor can be a mini servo motor. Mechanical actuation could encompass, for example, the use of tendons to drive the probe deployment arrangement. In other embodiments, the probe deployment arrangement comprises an inflatable member arranged to inflate when the probe deployment arrangement is actuated, the inflatable member being arranged to move the probe along a direction radially outwards from the longitudinal axis of the guide member as the inflatable member inflates. In some embodiments, the inflatable member can be inflated until a desired pressure between the probe and the cavity wall is reached. This arrangement may facilitate an improved orientation of the probe with respect to the cavity wall and an improved control of the pressure between the probe and the cavity wall. The applied pressure and probe orientation may also be more comparable between different positions in the lumen, which may improve the consistency of the measurements. Additionally, this arrangement may facilitate conformity or adaptation of the apparatus to the shape of the lumen in which the guide member is deployed.

To inflate the inflatable member pneumatically, a combination of gas conduits and valves are provided. These conduits may transport air, or pure carbon dioxide, or another gas. Optionally, there are at least two air conduits: a main pressurised air source and one pressure relief line, wherein each inflatable member has an internal micro valve to control the inflation of the inflatable member. Alternatively, each inflatable member has an air conduit and an external valve to control the inflation of the inflatable member. In other embodiments, the actuation is hydraulic and a liquid such as water or saline could be used to inflate the bellows. Another liquid could also be used.

The probe deployment arrangement may be resiliently biased to move the probe radially inwards to a resting position, for example along a radius. This can provide a fail-safe mechanism, which ensures that if actuation of the probe deployment arrangement ceases or, for example, the tendon or motor used to actuate the probe deployment arrangement fails, the probe does not remain extended radially outwards in its deployed position. Instead, the probe will contract towards the guide member so that the apparatus can be safely removed without causing damage to a patient.

In some embodiments, the probe comprises a sensor arranged to detect a property of a cavity in which the guide member is deployed. The sensor may be for example, but not limited to, an optical sensor, an electronic sensor, or a multispectral optoelectronic sensor. When the probe is an optical sensor, reflected light may be collected by the optical sensor, and the signal is routed via optical fibres to a, for example, CCD detector located external to the cavity in which the guide member is deployed. Optical sensors, such as optical fibres, can require a uniform contact between the probe and the lumen; preferably, the surface of the optical sensor is parallel to the wall of the cavity. Similarly, optoelectronic sensors can require the surface of the sensor to be parallel to the wall of the cavity. Advantageously, by deploying the probe along a direction radially outwards from the longitudinal axis of the guide member, the device may facilitate achieving this required good contact between the probe and the tissue.

Alternatively, the probe may be an optical probe (using fluorescence or structured light), and optoelectronic probe (for example, using multispectral photodiodes or optical coherence tomography), a non-optical probe (for example, ultrasound), or the probe may be a mini camera which generated traditional images or could be used for DRS. In embodiments where the probe is an optoelectronic sensor, diffuse reflectance spectroscopy (DRS) may be used to scan the cavity in which the guide member is deployed. The probe, which may be an optical fibre, can collect light reflected off the wall of the cavity and route it to an in-situ detector or detectors for electronic processing. The detector may then transmit the results as wired or wireless electronic signals. This optoelectronic sensor can be advantageous in comparison to purely optical sensors coupled with optical fibres, as it may reduce the mechanical and space constraints of routing multiple optical fibres to an external detector.

In some embodiments, the probe comprises, in addition to or instead of a sensor, a nozzle for spraying a liquid in the cavity in which the guide member is deployed. Probes may combine sensors and nozzles or separate respective probes may be provided. In these embodiments, the addition of deployable distal and proximal (relative to the tip of the guide member) balloons to the apparatus may be required to seal the area and optimise the application of the solution to the lumen wall. Additionally, a suction conduit may be required to evacuate any excess liquid, which may accumulate in one area of the cavity, for example due to gravity. Advantageously, the probe may be used to homogeneously wash, or apply biological markers to, an area of the wall of a tubular organ.

The apparatus may comprise a plurality of probes or a plurality of probe deployment arrangements arranged around the guide member with rotational symmetry. Each probe or probe deployment arrangement may operate independently of the other probes or probe deployment arrangements. This may facilitate the device adapting to variations in the geometry of the lumen, which are often not perfectly cylindrical. The guide member may act as a structural base or stabilising axis. By deploying multiple probes, the device may centre itself in the lumen. This may help to stabilise the device and may facilitate an equal pressure between each probe and the cavity in which the guide member is deployed.

Furthermore, the apparatus may comprise a rotating arrangement for rotating the probe, the plurality of probes, the probe deployment arrangement or the plurality of probe deployment arrangements relative to the guide member. This arrangement may be advantageous, as rotational symmetry means only partial rotation, rather than a complete rotation, of the apparatus is required to scan the whole circumference of a section of the lumen. Such a radial array of probes may facilitate quicker scanning and therefore shorter procedures. In some embodiments, the probes or probe deployment arrangements may be arranged such that the entire circumference of the wall may be imaged without rotation. A rotating arrangement is, however, arranged with a single probe or probe deployment arrangement in some embodiments. In embodiments where the apparatus comprises a drive arrangement and a rotating arrangement, the device can be moved along the guide member; this allows scanning of the entire interior of the tubular organ in which the guide member is deployed.

The apparatus may comprise an inflatable torus disposed around the guide member, wherein the inflatable torus is arranged to inflate radially away from the longitudinal axis of the guide member when inflated. One or more probes may be secured to the inflatable torus and may be deployed when the inflatable torus is inflated. Inflation of the inflatable torus may occur until a predetermined pressure between the inflatable torus and the wall of the cavity in which the guide member is deployed is reached. The apparatus may further comprise a second inflatable torus, wherein the one or more probes or probe deployment arrangements are disposed between the two tori. Once inflated, the tori may act as tissue stabilisers in the area around the apparatus. Advantageously, this may facilitate a better contact between the probes and the tissue. In turn, a better contact may facilitate faster scanning by the probes and an improved scan result. A further advantage is that the inflatable tori may stabilise the tissue and thereby may facilitate improved image processing and analysis. In some embodiments, more than two inflatable tori can be disposed around the guide member.

In some embodiments, the entire device, including the one or more tori described above may be disposed within a balloon, wherein the guide member extends through the balloon at either end of the device. The balloon may protect the electronics of the device from damage, for example from moisture inside the tubular organ. The balloon may stabilise the tissue of the cavity in which the guide member is deployed, which may facilitate improved scan results. In other embodiments, a transparent stretchable membrane may be disposed between two inflatable tori such that when the tori are inflated, the membrane is stretched between the two tori. An edge of the membrane may be secured to one of the inflatable tori and an opposing edge of the membrane may be secured to the second inflatable tori. In this arrangement, the membrane may be easily deployed when the two inflatable tori are inflated. The deployed membrane may then facilitate stabilising of the tissue of the wall of the cavity in which the guide member is deployed.

In some embodiments, the balloon or membrane may be a carrier of a probe or probes. In this arrangement, the balloon or membrane may act as a probe deployment arrangement. When the balloon is inflated or the membrane is deployed, the probe or probes secured to the balloon or membrane are deployed. This arrangement may facilitate tissue stabilisation in the same location as the probe deployment and reduce the number of components.

The pressure exerted by the one or more inflatable tori on the wall of the cavity can be controlled by increasing or decreasing the volume of a fluid inside the torus. The volume can be controlled in the same way as the inflation of the inflatable member is controlled; for example, with conduits and values. In some embodiments, increasing the volume of the fluid (for example a gas such as carbon dioxide or air, or a liquid such as water or saline) can increase the diameter of the torus until a desired pressure is reached between the torus and the wall of the cavity in which the guide member is deployed. At this point, actuation can cease. The pressure should be below the prescribed safety threshold which can be found in the literature. Alternatively, a collar or a snare may be placed around the one or more tori to fix their diameter. Once a torus is inflated to the set diameter, the rigidity of the torus can continue to increase as the volume of the fluid inside the torus increases, whilst the diameter does not increase beyond the set diameter. This arrangement is advantageous as it may facilitate a reduction in tissue deformation whilst sufficiently stabilising the tissue.

The guide member of the first, second and third aspects may be a flexible and/or steerable guide wire, for example an endoscope. In some embodiments, the guide member may be a catheter or an endoscope like device without the capacity for imaging. The guide member may be inserted into an anatomical cavity through an incision or a natural orifice. When the guide member is an endoscope, the endoscope may be configured for use in a tubular organ, for example a colon or a bowel. However, the apparatus described above could also be used in conjunction with other tubular anatomical sites such as blood vessels. The apparatus may be small enough to be used inside small or medium sized blood vessels, not just the aorta or venae cavae and their primary branches. The apparatus could be used for intravascular imaging, to apply drugs to atherosclerotic plaque, or to aspirate atherosclerotic plaque. Alternatively, the apparatus could be used to perform intravascular tissue engineering (for example to repair or replace the internal lining of a blood vessel). The apparatus of the first, second and third aspects could also be used in conjunction with other types of tubular structures in other applications, for example pipeline inspection. The pipelines may be, for example but not limited to, drainage pipes, oil pipelines, or pipes for mining purposes.

The apparatus of any of the aspects described above may be fixed relative to the guide member, or the apparatus may be moveable relative to the guide member.

BRIEF DESCRIPTION OF THE DRAWINGS

Embodiments of an endoscopic probe device will now be described with reference to the accompanying drawings, in which.

DETAILED DESCRIPTION

Figure 1:
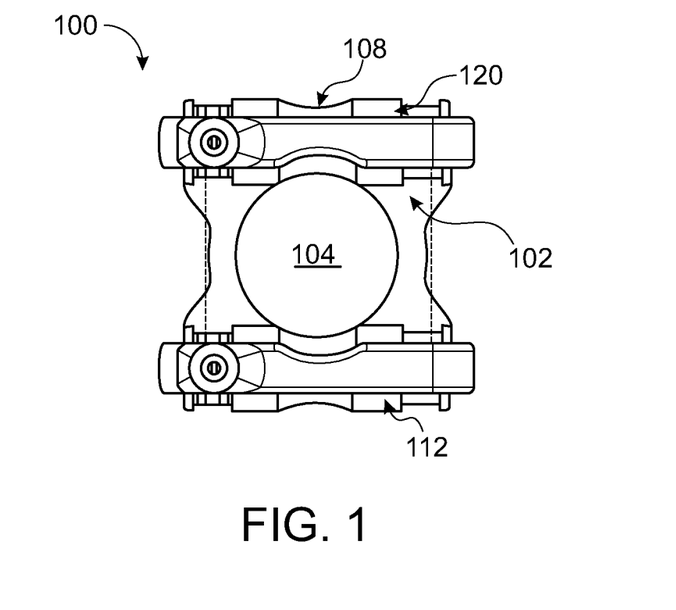
FIG. 1 illustrates a top view of an endoscopic probe device.
Figure 2:
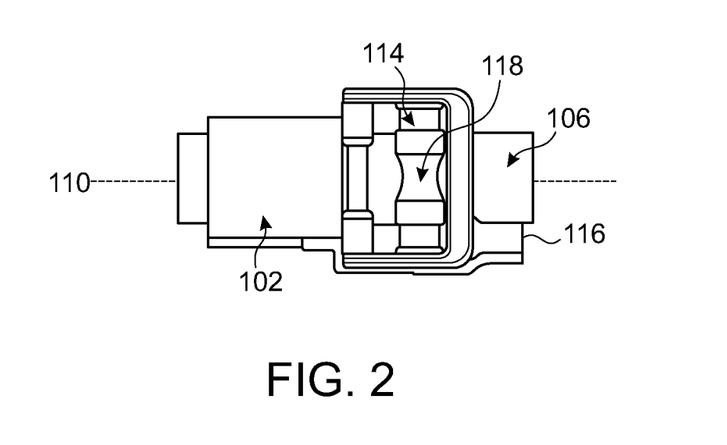
FIG. 2 illustrates a side view of the endoscopic probe device illustrated in FIG. 1, illustrating the arrangement of the endoscopic probe device and an endoscope.

With reference to FIGS. 1 and 2, an endoscopic probe device 100 comprises a body 102 having a cavity 104 for receiving an endoscope 106. The endoscopic probe device 100 further comprises a drive arrangement 108. The drive arrangement 108 is arranged to move the body 102 along the endoscope 106. With reference specifically to FIG. 2, an endoscope 106 is disposed through the cavity 104 of the body 102. The endoscope 106 has a longitudinal axis 110, the orientation of which is indicated by the dotted line in FIG. 2. The endoscopic probe device 100 is arranged to move along the endoscope 106 in a direction parallel to the longitudinal axis 110.

The drive arrangement 108 comprises two rotating members 112 which are coupled to the body 102 and arranged to frictionally engage the endoscope 106 on opposite sides of the endoscope 106. Each rotating member 112 comprises a capstan 114 and a rolling surface 118. A tendon 116 engages each capstan 114 to drive the drive arrangement 108. The tendons 116 transmit a force, for example a force exerted by a user, or another actuation mechanism such as a motor, to the capstan 114. The force exerted by the tendons 116 causes the capstan 114 to rotate, thereby turning the rolling surface 118 of the rotating members 112 and translating the endoscopic probe device 100 along the endoscope 106. In some embodiments the one or more rotating members 112 are actuated by respective motors coupled to the rotating members 112. Preferably, the motors are micro electric motors. The motors can be directly coupled or indirectly coupled, for example via a gear box or other components, to the one or more rotating members 112. In some embodiments, a single motor drives both the rotating members 112 via a suitable transmission arrangement.

The endoscopic probe device 100 also comprises a measurement arrangement 120 for obtaining a position of the body 102 relative to the endoscope 106. The measurement arrangement 120 is a rotary encoder mounted on an axle of one of the one or more rotating members 112. The measurement arrangement 120 is configured to determine the number of rotations of the one or more rotating members 112 in order to obtain the displacement of the body 102 along the endoscope 106. Alternatively, a measurement arrangement 120 may be mounted on an axle of each of the one or more rotating members 112. The measurement arrangement transmits encoder pulses to a position detection unit, either via a wire or wirelessly. The position detection unit may be coupled to the body or provided separately.

Figure 3:
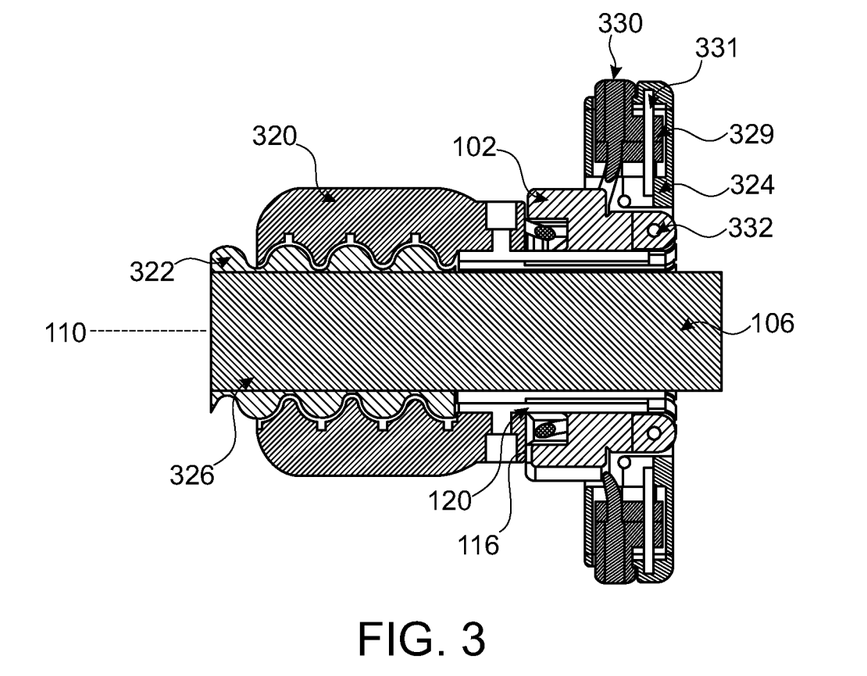
FIG. 3 illustrates another endoscopic probe device.

With reference to FIG. 3, the drive arrangement 108 comprises a transmission member 322 coupled to the body 102. The coupler 320 is arranged to couple the body 102 and the transmission member 322. The transmission member 322 is a sheath which accepts the endoscope. The sheath moves the body 102 relative to the endoscope in response to an external force. The sheath could be actuated by a user, or actuated through the use a motor. The sheath is sufficiently stiff axially to translate the body 102 relative to the endoscope 106. The sheath also has sufficient torsional rigidity to rotate the body 102 relative to the endoscope 106 in some embodiments. In this embodiment, the measurement arrangement 120 is an optoelectronic sensor coupled to the body 102 and configured to determine the displacement of the body 102 along the endoscope surface, using the gradations 326 on the endoscope as a reference. Alternatively, in other embodiments which use the transmission member 322, the measurement arrangement 120 may obtain the position and orientation of the body 102 by comparing the position of the transmission member 322 to a reference point. This comparison could be performed automatically by a position detection unit, for example using optical sensors, or by a user. The orientation of the body 102 relative to the endoscope 106 is determined by the measurement arrangement 120 using optical sensors. In some embodiments, alternative sensors, for example optical flow sensors (used in optical computer mice for example), potentiometric sensors or Hall Effect sensors over multipole strip magnets, are used.

With further reference to FIG. 3, the apparatus comprises a scanning head 329 carrying a probe 330. The probe 330 is disposed through and secured to the scanning head 329. The scanning head 329 is held inside a probe deployment arrangement 324 by a rod 331 such that it rides along the rod 331. A compression spring acting as a resilient member (not shown) is disposed around the rod 331. The scanning head 329 is resiliently biased radially outwards by the compression spring when the probe deployment arrangement 324 is deployed. The compression spring is arranged to maintain a pressure between the probe 330 and a wall of a cavity in which the endoscope is deployed and designed to prevent pressures on the wall of the cavity exceeding a prescribed safety threshold. These thresholds can be found in the literature for a variety of different tubular organs such as the colon. A stream of pressurised gas, for example carbon dioxide, may also be used to fill a cavity between the scanning head 329 and the probe deployment arrangement 324. The pressurised cavity can act as a resilient member in combination with, or instead of, the compression spring.

The probe deployment arrangement 324 is secured to the body 102 by a pivot 332. A tendon pull arrangement (not shown) is provided to deploy the probe deployment arrangement 324 by pivoting it outwards about the pivot 332. The probe deployment arrangement 324 can be retracted using the tendon pull arrangement to cause rotation inwards. The probe deployment arrangements 324 are deployed from a rest position and are resiliently biased towards the rest position. In the rest position, the probe deployment arrangements 324 lie parallel to the longitudinal axis of the endoscope 110.

The probe deployment arrangement may incorporate a prismatic joint with hydraulic or pneumatic actuation. This may facilitate the probe being deployed to different radial distances from the endoscope. By considering changes in the signal from the probe, it may be possible to detect contact between the probe and the wall of the cavity in which the endoscope is deployed (for example, if the probe is configured for use in diffuse reflectance spectroscopy (DRS), the signal may increase to a maximum when the probe touches the wall of the cavity). The prismatic joint may be configured to maintain the probe at a predetermined distance from the wall of the cavity or at a distance where a predetermined fraction of the maximum signal is measured by the probe. This arrangement may facilitate improved consistency in the output of different probes. In other embodiments, there may be a plurality of probe deployment arrangements arranged around the endoscope. Each probe deployment arrangement may be deployed at a different angle. This may facilitate a variable deployment diameter of the apparatus. Each probe may be mounted on a compliant shoe, which may facilitate a parallel contact between the surface of the probe and the wall of the cavity in which the endoscope is deployed regardless of the angle of deployment of the respective probe deployment arrangement.

The probe 330 is an optical fibre which delivers light to an area of interest in the cavity and collects the light reflected off the cavity in which the endoscope is deployed, for example for use in diffuse reflectance spectroscopy (DRS). Optical fibres need good contact with the tissue; preferably the surface of the optical sensors is substantially parallel to the wall of the cavity. In this embodiment, a good contact is achieved through the use of the compression spring. To reduce stresses on the optical fibres due to bending, the optical fibres follow a curved path around the apparatus, curving in a circumferential direction around the body 102 as the optical fibres extend along the longitudinal direction 110, to increase a bending radius of the optical fibres. Each fibre is routed away from the apparatus along a recessed channel in the coupler 320 to a detector, which may be a CCD detector, for processing. This combination of an optical fibre and a detector can be referred to as an optical fibre probe. In some embodiments, the detector is located external to the apparatus. In other embodiments, it is located on the apparatus.

In some embodiments, a prism, grating, or similar dispersion or diffraction arrangement is provided in combination with the optical fibres to disperse or diffract the emitted light into different wavelengths. The optical fibres route the collected light to a detector which comprises spectral sensors. Alternatively, a multispectral photodiode array chip may be used. Each diode has a filter for a certain range of wavelengths and therefore a dispersion or diffraction arrangement is not required. The detector may be a CCD detector or a complementary metal-oxide-semiconductor (CMOS) detector. The detector then processes the results electronically. The detector transmits the data as electronic signals, wirelessly or through wires. This combination of an optical fibre and a detector comprising spectral sensors provides a multispectral optoelectronic probe. In other embodiments, the probe can be a purely electronic sensor to measure, for example, impedance. Alternatively, the probe may be an optical probe, wherein the probe comprises an optical sensor and the associated electronics for processing in an integrated circuit. In other embodiments, the probe may be a camera or an ultrasound transducer or receiver.

With further reference to FIG. 3, the apparatus comprises a plurality of probes 330 and probe deployment arrangements 324 arranged around the apparatus with rotational symmetry. Therefore, the body 102 does not need to complete an entire rotation in order to scan around the circumference of the lumen. In other embodiments, only one probe deployment arrangement 324 is provided.

Figure 4:
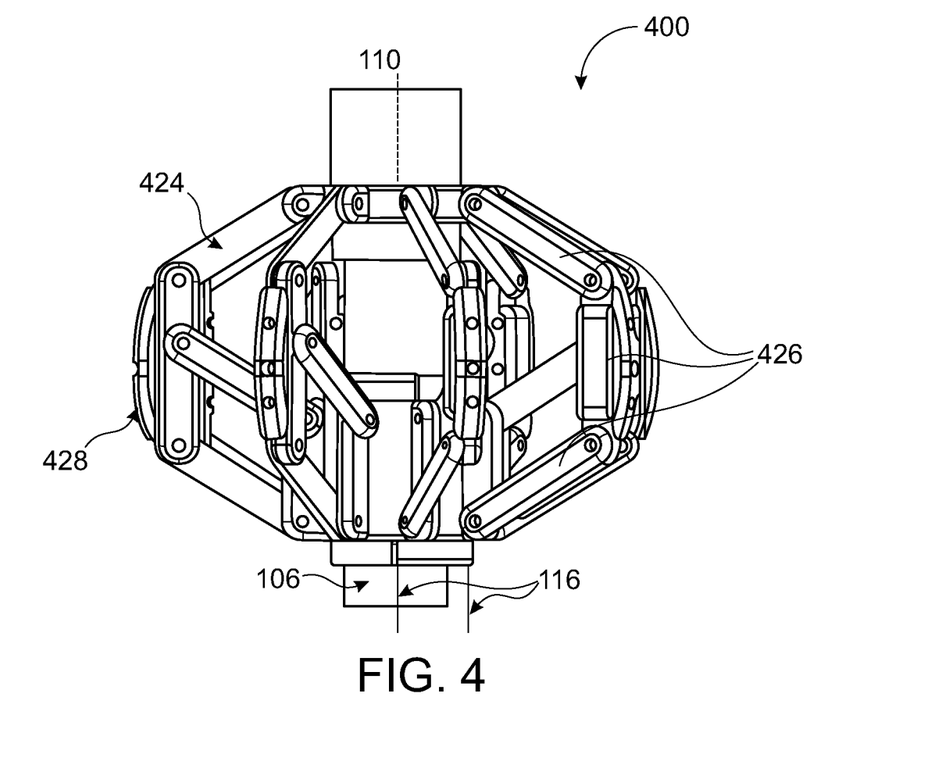
FIG. 4 illustrates a probe deployment arrangement.

With reference to FIG. 4, an alternative endoscope probe device 400 comprises a probe deployment arrangement 424. In some embodiments, the probe deployment arrangement 424 of FIG. 4 is combined with the drive arrangements 108 of the endoscopic probe devices illustrated in FIGS. 1 to 3. In other embodiments, the probe deployment arrangement 424 is an attachment for an endoscope or can be incorporated into an endoscope. The endoscopic probe device 400 comprises a plurality of probe deployment arrangements 424. Each probe deployment arrangement 424 comprises a plurality of bars 426 which are connected in a parallel linkage. In some embodiments, the plurality of bars are connected in a planar linkage. Each probe deployment arrangement 424 comprises a resilient member 428 and a probe 430 secured to the probe deployment arrangement 424.

The probe deployment arrangement 424 is arranged to deploy the probe 430 along a direction radially outwards from a longitudinal axis 110 of the endoscope 106 by moving the probe 430 along a direction radially outward by virtue of the movement of the parallel linkage. As the ends of the parallel linkage are moved toward one another, the probe is deployed along a direction radially outwards from the longitudinal axis 110 of the endoscope 106. When the ends of the parallel linkage are moved away from one another, the probe is moved along a direction radially inwards towards the endoscope 106. In this embodiment, actuation of the probe deployment arrangement 424 is mechanical. The actuation can be by tendons 116. In other embodiments, actuation may be by mini servo motors. Alternatively, actuation may be hydraulic or pneumatic. The apparatus 400 further comprises a rotating arrangement for rotating the probe deployment arrangements 424 relative to the endoscope. In this embodiment, the rotating arrangement comprises two concentric tubes of different radii, wherein an internal tube is disposed inside an external tube and the endoscope 106 is disposed through the internal tube. When the rotating arrangement is actuated by tendons 116, the external tube rotates relative to the internal tube. The probe deployment arrangements 424 are secured to the external tube; therefore, as the external tube rotates, the probe deployment arrangements 424 also rotate.

The resilient member 428 provides a passive spring loading system. Preferably, the resilient member 428 should be configured to apply a pressure on the cavity wall that does not exceed the predetermined safety threshold and more preferably, the resilient member 428 should apply pressures to the cavity wall in a range much lower than the threshold for safety.

FIG. 4 illustrates only the probe deployment arrangement 424 and the probes are not shown. Any of the probes described above can be combined with the probe deployment arrangement 424. For example, the probe may be an optical fibre probe, a multispectral optoelectronic probe, an optical probe, or an electronic sensor.

Figure 5:
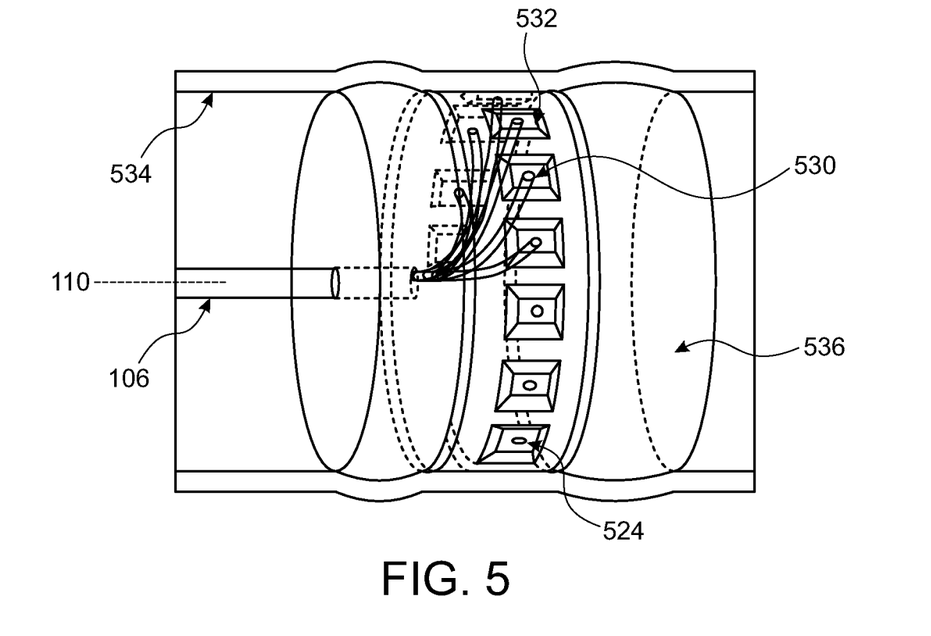
FIG. 5 illustrates another probe deployment arrangement.
Figure 6:
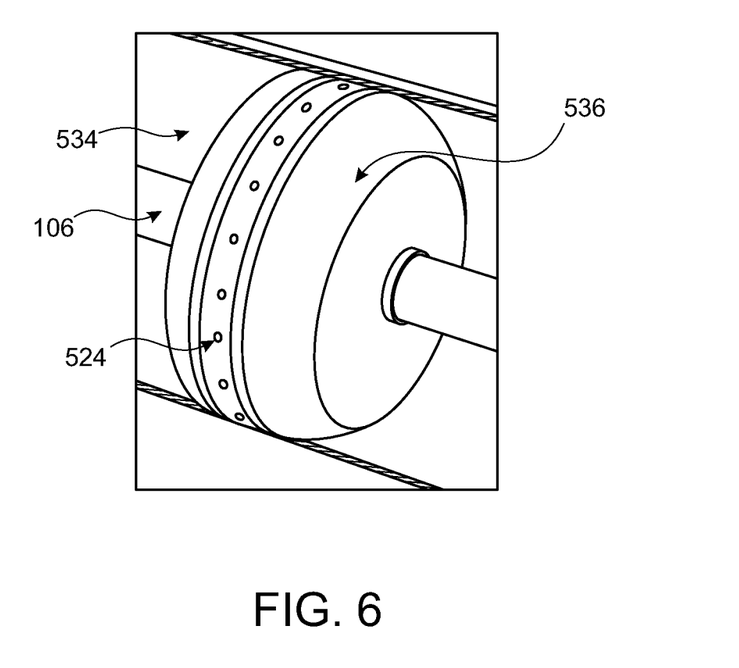
FIG. 6 illustrates another view of the probe deployment arrangement illustrated in FIG. 5.

With reference to FIGS. 5 and 6, an endoscopic probe device 500 comprises a probe deployment arrangement 524. The probe deployment arrangement 524 comprises an inflatable member 532 arranged to inflate when the probe deployment arrangement 524 is actuated. A plurality of probe deployment arrangements 524 are arranged around the endoscope 106 with rotational symmetry. Each probe deployment arrangement 524 carries a corresponding probe 530. As each inflatable member 532 is inflated, the probe 530 is deployed along a direction radially outwards from the longitudinal axis 110 of the endoscope 106. The probe 530 is an optical fibre probe. In other embodiments, any of the probes described above can be combined with the probe deployment arrangement 524. For example, the probe may be a multispectral optoelectronic probe, an optical probe, or an electronic sensor.

In some embodiments, the inflatable member 532 of each probe deployment member 524 can be inflated independently of the other inflatable members 532 of the plurality of probe deployment arrangements 524. This allows the apparatus to adapt to the shape of the cavity in which the endoscope is deployed and may ensure a good contact between the probe and the wall of the cavity 534, even when the tubular organ or lumen is irregularly shaped. In this embodiment, the inflatable member 532 is inflated pneumatically using gas conduits and valves, which are arranged to control the flow of gas into the inflatable member 532.

With reference to FIGS. 5 and 6, in some embodiments two inflatable tori 536 are disposed around the endoscope 106. Both inflatable tori 536 are arranged to inflate along a direction radially away from the longitudinal axis 110 of the endoscope 106 when actuated. The one or more inflatable tori 536 act as tissue stabilisers, stabilising the tissue along the wall of the cavity in the area around the apparatus. In this embodiment, the pressure exerted by the one or more inflatable tori 536 on the wall of the cavity 534 is controlled by increasing or decreasing the volume of a fluid inside the torus. This mechanism is similar to that which controls the inflation of the inflatable member 532. In other embodiments, the diameter of the torus can be fixed with a snare or a collar. The pressure exerted by the one or more inflatable tori 536 on the wall of the cavity 534 can then be controlled by increasing or decreasing the rigidity of the torus.

Figure 7:
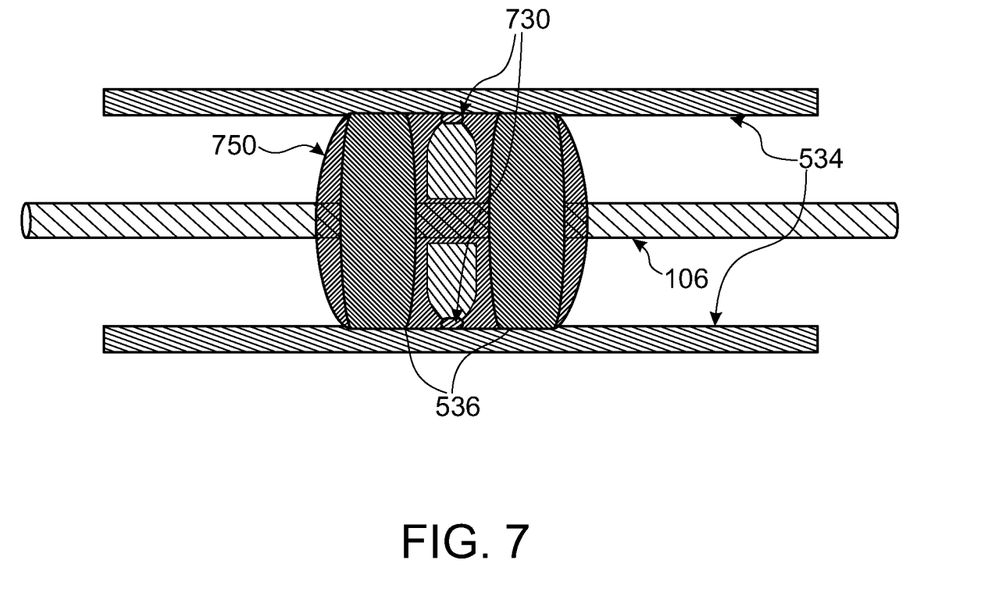
FIG. 7 illustrates another probe deployment arrangement.

With reference to FIG. 7, the entire device, including the tori described above, is enveloped by a balloon 750. The balloon may be a balloon such as that described in patent application GB1316333.2, the content of which is herein incorporated by reference. The balloon may facilitate stabilisation of the tissue of the cavity in which the guide member is deployed and/or may be configured to carry or support actuation means for the probe deployment arrangement and/or drive arrangement of the apparatus. Alternatively, the balloon 750 is arranged as a probe deployment arrangement, configured to carry and deploy the probes 730. In some embodiments, the balloon is arranged with the inflatable tori 536, as illustrated schematically in FIG. 7. When the inflatable tori 536 are inflated, the balloon 750 is pulled taut and brought into contact with the walls of the cavity 534 in which the endoscope 106 is deployed. In this manner, the probes 730 are deployed. In other embodiments, the balloon 750 is arranged without the inflatable tori 536. Actuation of the balloon is pneumatic, as described above with reference to the inflatable tori. Alternatively, actuation of the balloon 750 may be hydraulic. The probes 730 may be any of the probes described above. The balloon 750 may be formed of a thin, stretchable, membrane, or any other suitable material.

Figure 8:
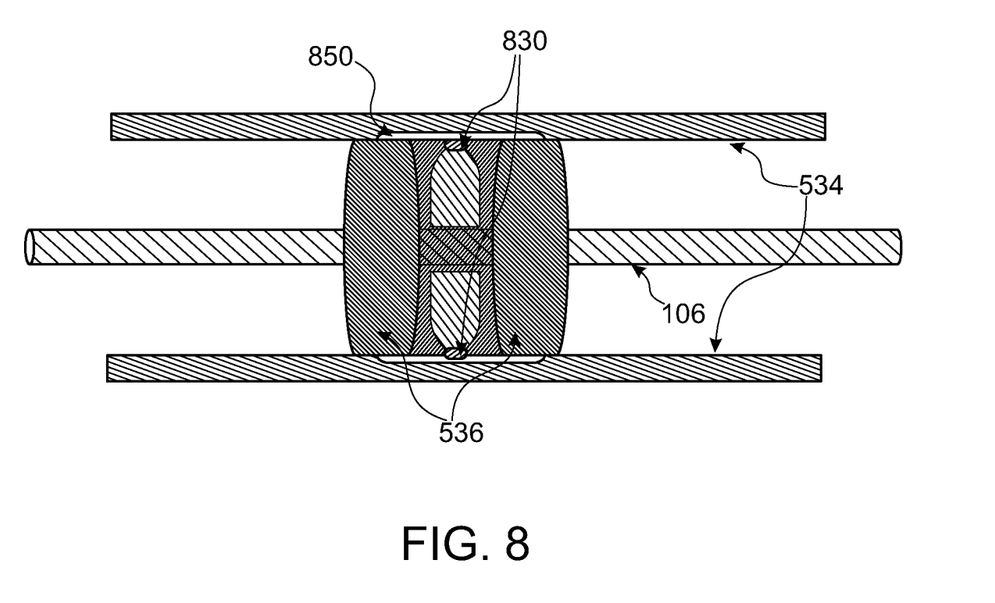
FIG. 8 illustrates another probe deployment arrangement.

In embodiments where the apparatus comprises the two or more inflatable tori, the balloon 750 is replaced with a membrane 850 which is disposed between and secured to the inflatable tori 536. This arrangement is illustrated schematically in FIG. 8. One or more probes 830 are secured to the membrane 850 and the membrane 850 is arranged to act as a probe deployment arrangement. The probes 830 may be any of the different types of probes described above. When the inflatable tori 536 are inflated, the membrane 850 is pulled taut and brought into contact with the walls of the cavity 534 in which the endoscope 106 is deployed. The probes 830 are therefore deployed by the membrane 850.

The probe deployment arrangements described above with reference to FIGS. 3 to 8 are, in some embodiments, resiliently biased to move the probe radially inwards to a resting position. The corresponding motion comprises a rotation about the pivot 332 in the case of FIG. 3 and motion substantially along a radius in the case of FIGS. 4 to 6. For example, the inflatable member described with reference to FIGS. 5 and 6 will begin to deflate if actuation ceased, thereby moving the probe away from the wall of the cavity. Similarly, the parallel linkage described with reference to FIG. 4 is arranged such that the ends of the plurality of bars move away from one another if actuation ceases, thereby moving the probe away from the wall of the cavity and towards the endoscope. The probe deployment arrangement described above with reference to FIG. 3 is, in some embodiments, resiliently biased to move the probe towards a resting position, wherein the probe deployment arrangement lies parallel to the longitudinal axis of the endoscope in the resting position. These are fail-safe mechanisms which ensure that the probe does not remain in its deployed position if any of the probe deployment arrangement actuation mechanisms fail. Consequently, the apparatus can be removed from a patient easily, without causing damage to the tissue of the wall of the tubular organ in which the endoscope is deployed.

While some specific embodiments have been described above, many variations, modifications, combinations and juxtapositions of the described features are possible and are included in this disclosure. Some examples are set out below.

For example, the probe or plurality of probes can be suitable for: obtaining a measurement, taking a sample of, or applying a substance to the wall of the cavity in which the endoscope is inserted. For example, the probes may be optical sensors, impedance sensors, or multispectral optoelectronic probes arranged to detect a property of the cavity in which they are deployed. Alternatively, the probes may be biopsy tools. However, the probe may be any other type of probe.

Alternatively, or additionally, the probe may comprise a nozzle for spraying a liquid in the cavity in which the endoscope is deployed. In this embodiment, additional components may be required on the apparatus. For example, if the probe were to comprise a nozzle for spraying a liquid, the probe could be used to homogenously wash an area or apply biological markers. The apparatus could then further comprise deployable distal and proximal (relative to the tip of the endoscope) balloons to seal the area and optimise the application of the solution and a suction probe to remove any excess liquid. This arrangement could be used for diagnostic purposes, for example fluorescence imaging, or for theranostic (a combination of diagnostic and therapeutic) purposes, for example a treatment whereby biological markers are applied to an area before infrared light is applied to the same are to burn the malignant tissue where the biological markers accumulate. The apparatus could also be used to prepare or chemically sterilise and isolate an area of a tubular organ for operations, for example a Natural Orifice Transluminal Endoscopic Surgery (NOTES) procedure in which an endoscope is passed through a natural orifice and internal incision rather than an external incision. For example the peritoneal cavity is accessed via the sigmoid colon for gallbladder and pancreatic surgery or through the oesophagus or stomach for surgery in the thorax area and peritoneal cavity.

In any of the embodiments described above, the apparatus may further comprise a rotating arrangement for rotating the probes or probe deployment arrangements relative to the endoscope. The rotating arrangement may be configured as described above with reference to FIG. 3. Alternatively, the rotating arrangement may be configured as described above with reference to FIG. 4.

The resilient member may be an active loading system, actuated by, for example but not restricted to, hydraulics or pneumatics. In an active system, the resilient member could comprise pressure or strain sensors. This would enable the force between the probe and the cavity wall to be measured, and the actuation of the resilient member altered in order to ensure that the pressure on the wall of the cavity does not exceed prescribed safety thresholds. These thresholds can be found in the literature for a variety of different tubular organs, for example the colon or bowel. In a passive spring loading or pressurised air design for the resilient member, the system can be designed to ensure that the threshold pressures of the cavity wall are not exceeded. Preferably, the resilient member should not allow a pressure on the cavity wall to exceed the tolerable threshold and ideally the resilient member should apply pressures to the cavity wall in a range much lower than the safety threshold.

The drive arrangements described with reference to FIGS. 1 to 3 may be combined with the pivotably coupled probe deployment arrangement described with reference to FIG. 3. The drive arrangement described with reference to FIGS. 1 to 3 may also be combined with the parallel linkage probe deployment arrangement described with reference to FIG. 4 or the probe deployment arrangements comprising the inflatable members described above with reference to FIGS. 5 and 6. For example, the drive arrangement and the probe deployment arrangement may be coupled end to end adjacent each other, in some embodiments.

The pivotably coupled probe deployment arrangement described with reference to FIG. 3 may be combined with the multispectral optoelectronic probe described previously. The multispectral optoelectronic probes can be carried by the scanning head secured disposed through the probe deployment arrangement. The probe deployment arrangement comprising inflatable members described with reference to FIG. 4, or the probe deployment arrangement comprising a parallel linkage described with reference to FIGS. 5 and 6, may also be combined with the multispectral optoelectronic probe described previously. The detector coupled to the optical fibres of the multispectral optoelectronic probe may be arranged on the apparatus or may be located outside of the body of the patient. Alternatively, the pivotably coupled probe deployment arrangement or any of the other probe deployment arrangements described above may be combined with an electronic sensor, an optical fibre probe, an optical probe, or the nozzle described previously.

Any of the above permutations of the probe and probe deployment arrangement may be combined with any of the drive mechanisms described with reference to FIGS. 1 and 2. Furthermore, any of the permutations described above may be combined with the inflatable torus described with reference to FIGS. 5 and 6. Additionally, any embodiment of the apparatus described above can be combined with any suitable guide member, for example a catheter or (steerable) guidewire and not only an endoscope.

Any of the probe deployment arrangements described above may be configured to facilitate a variable deployment distance. When a plurality of probe deployment arrangements are arranged around the guide member, each of the probe deployment arrangements may be actuated independently of the other probe deployment arrangements. Each of the plurality of probe deployment arrangements may be deployed independently to a different deployment distance to the one or more of the other probe deployment arrangements. Alternatively, each of the probe deployment arrangements may be deployed independently to an equal deployment distance. By configuring the actuation of each probe deployment arrangement, the apparatus may be fully adaptable to a range of organ or cavity geometries, not just tubular structures. This may facilitate use of the apparatus in asymmetrical lumens, for example the stomach.

Other variations and modifications will be apparent to the skilled person. Such variations and modifications may involve equivalents and other features which are already known and which may be used instead of, or in addition to, features described herein. Features that are described in the context of separate embodiments may be provided in combination in a single embodiment. Conversely, features which are described in the context of a single embodiment may also be provided separately or in any suitable sub-combination.

The invention claimed is:

1. An apparatus comprising:
   a guide member for insertion into an anatomical cavity along a longitudinal axis;
   a body defining a cavity for receiving the guide member therethrough;
   a drive arrangement for moving the body relative to the guide member;
   a probe for, in use, obtaining a measurement from, taking a sample of, applying a substance to, or applying a therapy to, an environment of the probe;
   a plurality of probe deployment arrangements for deploying the probe radially outwards from the longitudinal axis associated with the guide member, configured such that, when deployed, a deployment distance of a first one of the plurality of probe deployment arrangements is fixed relative to the guide member and independent of the deployment distance of the rest of the plurality of probe deployment arrangements; and
   a measurement arrangement including at least one of a rotary encoder, an optoelectronic sensor, an optical sensor, an optical flow sensor, or a potentiometric sensor, wherein the measurement arrangement is configured to measure a position of the body relative to the guide member disposed through the body.

2. The apparatus of claim 1, wherein the apparatus comprises a drive arrangement for moving the probe relative to the guide member.

3. The apparatus of claim 2, wherein the drive arrangement comprises one or more rotating members coupled to the body and arranged to engage the guide member to move the body along the guide member.

4. The apparatus of claim 3, wherein the one or more rotating members are arranged to move the body along the guide member by frictional engagement of the guide member.

5. The apparatus of claim 3, wherein the one or more rotating members are configured as a pinion or a worm gear, the pinion or the worm gear being arranged to move the body along the guide member by engaging a rack surface on the guide member.

6. The apparatus of claim 3, wherein the drive arrangement comprises a capstan and a tendon engaging the capstan for actuating the drive arrangement.

7. The apparatus of claim 3, wherein the drive arrangement comprises an electric motor for actuating the drive arrangement.

8. The apparatus of claim 2, wherein the drive arrangement comprises a transmission member coupled to the body and arranged to move the body relative to the guide member disposed through the body in response to a force applied to the transmission member.

9. The apparatus of claim 8, wherein the transmission member comprises a sheath for accepting the guide member, wherein the sheath is sufficiently stiff axially to translate the body relative to the guide member disposed through the body.

10. The apparatus of claim 9, wherein the sheath is sufficiently rigid torsionally to rotate the body relative to the guide member disposed through the body.

11. The apparatus of claim 1, wherein the probe deployment arrangement comprises a resilient member arranged to maintain a pressure between the probe and a wall of the cavity in which the guide member is deployed.

12. The apparatus of claim 1, wherein deploying the probe radially outwards from the guide member comprises deploying the probe along a direction radially outwards from a longitudinal axis of the guide member.

13. The apparatus of claim 12, wherein the probe deployment arrangement comprises a plurality of bars connected in a parallel linkage, the plurality of bars being arranged to move the probe along the direction radially outwards from the longitudinal axis of the guide member when the probe deployment arrangement is actuated.

14. The apparatus of claim 12, wherein the probe deployment arrangement comprises an inflatable member arranged to inflate when the probe deployment arrangement is actuated, the inflatable member being arranged to move the probe along the direction radially outwards from the longitudinal axis of the guide member as the inflatable member inflates.

15. The apparatus of claim 1, wherein the probe deployment arrangement is resiliently biased to move the probe radially inwards to a resting position.

16. The apparatus of claim 1, wherein the probe comprises an optical fibre secured to the probe deployment arrangement at one end to convey optical signals from the end at the probe deployment arrangement along the guide member, having a portion disposed along the guide member, the optical fibre being arranged to curve in a circumferential direction around the guide member and extend along a longitudinal direction of the guide member.

17. The apparatus of claim 1, wherein the probe comprises a sensor arranged to detect a property of the anatomical cavity in which the guide member is inserted.

18. The apparatus of claim 1, wherein the probe comprises a nozzle for spraying a liquid in the anatomical cavity in which the guide member is inserted.

19. The apparatus of claim 1, wherein the apparatus comprises a plurality of probes including the probe or the probe deployment arrangement comprises a plurality of probe deployment arrangements arranged around the guide member with rotational symmetry.

20. The apparatus of claim 1, wherein the apparatus comprises a rotating arrangement for rotating a plurality of probes including the probe relative to the guide member.

21. The apparatus of claim 1, wherein the apparatus further comprises:
an inflatable torus disposed around the guide member, wherein the inflatable torus is arranged to inflate radially away from the longitudinal axis of the guide member when actuated until a predetermined pressure between the inflatable torus and the wall of a cavity in which the guide member is deployed is reached.

22. The apparatus of claim 21, wherein the probe is one of a plurality of probes and at least some of the plurality of probes are secured to the inflatable torus and are deployed when the inflatable torus is inflated.

23. The apparatus of claim 21, wherein the apparatus further comprises a second inflatable torus, wherein the probe deployment arrangement is disposed between the tori.

24. The apparatus of claim 23, wherein a membrane is disposed around or between the two inflatable tori, such that, when the two inflatable tori are inflated the membrane is taut and in contact with the wall of the cavity in which the guide member is deployed.

25. The apparatus of claim 24, wherein the probe is one of one or more probes that are secured to the membrane and are deployed as the two inflatable tori are inflated and the membrane is pulled taut.

26. The apparatus of claim 1, wherein the probe is a multispectral optoelectronic probe further comprising a spectrograph.

27. The apparatus of claim 26, wherein the probe is arranged to employ diffuse reflectance spectroscopy.

28. The apparatus of claim 1, wherein the guide member is an endoscope.

29. The apparatus of claim 28, wherein the endoscope is for a colon or bowel exam.

30. The apparatus of claim 1, wherein the probe deployment arrangement is secured to the body.

31. The apparatus of claim 1, wherein the probe is configured to be secured to the probe deployment arrangement.

32. The apparatus of claim 1, wherein:
the probe is one of a plurality of probes; and
the probe deployment arrangement is configured for deploying, radially outwards from the guide member, the plurality of probes arranged around the guide member with radial symmetry.

33. An apparatus for attaching to a guide member for insertion into an anatomical cavity along a longitudinal axis, the apparatus comprising:
a body defining a cavity for receiving the guide member therethrough;
a drive arrangement for moving the body relative to the guide member;
a probe configured to be secured to the body for, in use, obtaining a measurement from, taking a sample of, applying a substance to, or applying a therapy to, an environment of the probe;
a plurality of probe deployment arrangements for deploying the probe radially outwards from the longitudinal axis associated with the guide member, configured such that, when deployed, a deployment distance of each of the plurality of probe deployment arrangements is independent of the deployment distance of the rest of the plurality of probe deployment arrangements, wherein a first probe deployment arrangement of the plurality of probe deployment arrangments is fixed relative to the guide member; and
a measurement arrangement for measuring a position of the body relative to the guide member disposed through the body.

34. The apparatus for attaching to the guide member for insertion into an anatomical cavity as claim 33 recites, wherein:
the probe is one of a plurality of probes; and
the probe deployment arrangement is configured for deploying, radially outwards from the guide member, the plurality of probes arranged around the guide member with radial symmetry.

* * * * *